United States Patent [19]
Karakelle et al.

[11] Patent Number: 5,302,392
[45] Date of Patent: Apr. 12, 1994

[54] POLYURETHANE SPONGE HAVING RAPID IODINE RELEASE

[75] Inventors: Mutlu Karakelle, Spring Valley; C. David Benson, Waynesville; Robert A. Taller, Centerville; Min-Shiu Lee, Spring Valley, all of Ohio; Mohammad A. Khan, Sandy, Utah

[73] Assignee: Becton, Dickinson and Company, Franklin Lakes, N.J.

[21] Appl. No.: 570,656

[22] Filed: Aug. 20, 1990

[51] Int. Cl.$^5$ .................... C08G 18/10; A61M 31/00
[52] U.S. Cl. .................... 424/409; 424/78.27; 424/78.25; 604/265
[58] Field of Search ............. 424/80, 409, 411, 78.25, 424/78.27; 604/369; 132/286; 206/209, 569

[56] References Cited

U.S. PATENT DOCUMENTS

| | | | |
|---|---|---|---|
| Re. 32,991 | 7/1989 | Szycher et al. | 424/411 |
| 3,094,494 | 6/1963 | Hopkins et al. | 604/369 |
| 3,127,312 | 3/1964 | Boyer | 424/411 |
| 3,235,446 | 2/1966 | Shelanski et al. | 167/17 |
| 3,759,375 | 9/1973 | Nappi | 132/286 |
| 3,977,406 | 8/1976 | Roth | 604/369 |
| 4,373,009 | 2/1983 | Winn | 604/280 |
| 4,381,380 | 4/1983 | LeVeen et al. | 525/452 |
| 4,642,267 | 2/1987 | Creasy et al. | 428/413 |
| 4,769,013 | 9/1988 | Lorenz et al. | 167/17 |

OTHER PUBLICATIONS

Schenck et al. *Journal of Pharmaceutical Sciences*, 68, 1505, 1979.

Primary Examiner—Thurman K. Page
Assistant Examiner—Peter F. Kulkosky
Attorney, Agent, or Firm—Richard E. Brown

[57] ABSTRACT

A polyurethane composition has particles of solid polyvinylpyrrolidone-iodine complex evenly distributed throughout the polyurethane matrix so that the complex does not associate with the polyurethane to any appreciable extent. In one embodiment of the composition, the polyurethane is thermoplastic for coating or molding applications. In another embodiment, the composition is a polyurethane foam particularly useful as a sponge for scrubbing which provides almost instantaneous release of the complex. The sponge may be provided in a package which includes other items useful for scrubbing.

23 Claims, 4 Drawing Sheets

POLYURETHANE SPONGE HAVING RAPID IODINE RELEASE

BACKGROUND OF THE INVENTION

1. Field of the Invention.

This invention relates to germicidal compositions, and more particularly relates to an improved dry germicidal sponge.

2. Background.

Iodine is a well-known germicide with activity against a wide range of bacteria and viruses, and much effort has been directed to finding satisfactory vehicles for its administration. Carriers of iodine, often termed iodophors, are generally polymeric materials which form complexes with iodine. Polyurethanes are disclosed as iodophors by Shelanski in U.S. Pat. No. 3,235,446 and by LaVeen in U.S. Pat. No. 4,381,380.

Polyvinylpyrrolidone (povidone, PVP) is a well known iodophore which forms a stable complex with iodine (hereinafter P-I). This complex has been extensively used in germicidal preparations such as aerosols, ointments and cleansing compositions for topical application. The structure of P-I is discussed by Schenck et al. in the *Journal of Pharmaceutical Sciences* 68, 1505 (1979).

Lorenz et al. in U.S. Pat. No. 4,769,013 discloses an interpenetrating polymer network (IPN) foam complex of PVP and polyurethane which absorbs iodine from an aqueous solution and then releases the iodine slowly when the dry sponge is contacted with water.

Although not concerned with iodine delivery, Creasy, in U.S. Pat. No. 4,642,267 and Winn, in U.S. Pat. No. 4,373,009 disclose complexes of polyurethane and PVP. In the Creasy et al. patent, a blend of PVP and polyurethane is applied to a substrate surface as a hydrophilic coating. In the Winn et al. patent, a copolymer of povidone with a hydroxyethyl acrylate is applied as a lubricious coating to a substrate surface by first priming the surface with an isocyanate and then reacting the isocyanate with the copolymer.

Iodophor-iodine complexes have been impregnated into a sponge or brush used for germicidal cleaning or scrubbing. Often, such implements are included in a kit of materials which may also include other items useful for patient preparation, such as towels, gloves and the like. Prior art iodophors and iodine complexes made therefrom suffer from various deficiencies such as instability leading to loss of iodine titer and tissue sensitivity due to the corrosive effects of iodine. On the other hand, the complex of polyurethane and P-I of U.S. Pat. No. 4,769,013, because of the IPN nature of the patented product, delivers iodine too slowly to be useful in a sponge for surgical scrubbing.

While the above disclosures have improved the delivery of iodine, further improvements, particularly an iodine carrier complex providing substantially instantaneous delivery of iodine is needed. The present disclosure is directed to fulfillment of this need.

SUMMARY OF THE INVENTION

A composition has solid particles of a water soluble complex of a polymer and a germicidal agent evenly dispersed throughout a polyurethane. Because the complex is a solid particle, it does not form a molecular association with the polyurethane so that, when the composition is contacted with water, the water soluble particles dissolve for rapid availability of the germicidal agent.

Suitable water soluble polymers are polyethylene oxide (PEO) and PVP. Representative suitable germicidal agents are chlorhexidine gluconate and iodine. The preferred complex is P-I.

The most preferred composition is a polyurethane foam having the P-I particles dispersed in the foam matrix. The preferred polyurethane is the reaction product of an aromatic diisocyanate, polypropylene oxide glycol (PPG) and water.

Another embodiment of the composition of the invention is a thermoplastic polyurethane containing the P-I particles. In this form, prepared from a diisocyanate, polyether glycol and diol chain extender, the composition of the invention is useful as a germicide releasing coating on a medical article, such as a catheter, or as a molded bristle useful as a component of a brush.

Another aspect of the invention is a package of materials useful for surgical scrubbing which includes the sponge or brush. Other components which may optionally be included in the package are a nail cleaner, a wipe and a detergent. If desired, a powder or liquid detergent may be impregnated into the sponge.

Thus, the invention provides a sponge or brush for surgical scrubbing which includes a germicidal agent in a form which facilitates substantially instantaneous release when the scrub is contacted with water or an aqueous detergent. Because of the rapid release, an aqueous solution brought into contact with the scrub reaches an antimicrobially effective level of germicide in a matter of seconds, in contrast to prior art polyurethane P-I germicidal sponges which require a much longer time to become effective. The advantage to a surgeon of not having to wait before starting to scrub is immediately evident.

The dry pack sponge or brush of the invention provides a further advantage over prior art P-I preparations in overcoming the well known loss of iodine titer which occurs in prior art preparations as a result of the reaction of iodine and water to give iodide ion. In the prior art, the iodine is introduced into the foam as an aqueous triiodide solution. This procedure requires a time consuming drying procedure during which time iodine is being converted to iodide. The solid particles of P-I of the present invention do not contact water until ready for use so that the iodine titer remains substantially unchanged during storage.

DETAILED DESCRIPTION

Figure 1:
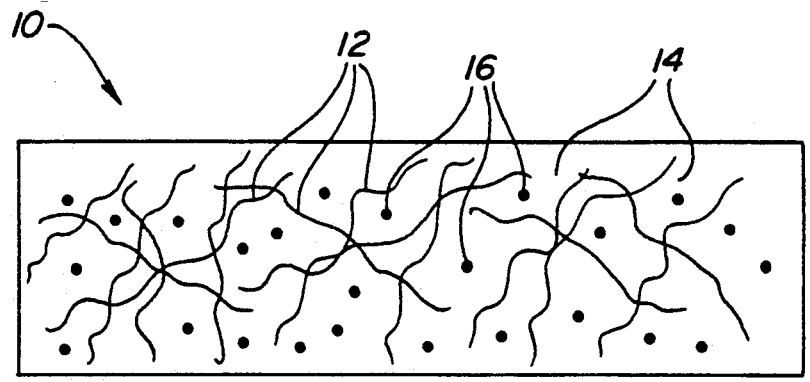
FIG. 1 illustrates a sponge of the invention having particles of solid P-I therein.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, a polyurethane foam sponge containing granules of solid P-I is provided. The P-I and the polyurethane are substantially uncomplexed so that when the sponge is contacted with water, an almost instantaneous release of the P-I into the water occurs.

The components of the sponge will first be described followed by details of the method for its preparation.

The flexible polyurethane foam sponge of the invention may be synthesized from a polyisocyanate, a polyglycol, a blowing agent, and the solid P-I particles as described below. A chain extender may be included. In addition, the foam may also contain a foam stabilizer catalyst, emulsifier, cell size regulator, supplemental blowing agent and other conventional additives such as fillers, flame retardants, emollients, colorants, fragrances and the like.

Preferred polyisocyanates are diisocyanates. Suitable diisocyanates are aromatic diisocyanates such as 4,4'-diphenylmethane diisocyanate (MDI), toluene diisocyanate (TDI) and 3,3'-diphenylmethane diisocyanate, alicyclic diisocyanates such as isophorone diisocyanate and 4,4'-dicyclohexylmethane diisocyanate, and aliphatic diisocyanates, as, for example, hexamethylene diisocyanate. The preferred diisocyanates are MDI and TDI. The most preferred diisocyanate is an 80/20 mixture of 2,4-TDI and 2,6-TDI.

A conventional polyglycol component, di, tri or multifunctional, which may be used is a polyester glycol, a silicone glycol, a fluorinated glycol or preferably a polyether glycol or mixtures thereof. Suitable polyester glycols are, for example, polycaprolactone and polyethylene adipate. Suitable silicone glycols are, for example, polydimethylsiloxane glycols such as Q4 3667 available from Dow Corning Corp.

The preferred polyether glycol may be polyethyleneoxide glycol (PEG), polytetramethyleneoxide glycol, (PTMEG), polypropyleneoxide glycol (PPG) or mixtures or copolymers thereof. The most preferred glycol is PPG having a molecular weight of about 1,000 to 2,000. These products are available commercially under the trade names Multranol TM (Mobay Co., Pittsburgh, Pennsylvania) and Voranol TM (Dow).

The chain extender may be water, a low molecular weight branched or unbranched diol, diamine or aminoalcohol of up to 10 carbon atoms or mixtures thereof. Representative nonlimiting examples of chain extenders are water, BDO, ethylene glycol, diethylene glycol, triethylene glycol, 1,2-propanediol, 1,3-propanediol, 1 6-hexanediol, trimethylol propane, 1,4-bis-hydroxymethyl cyclohexane, hydroquinone dihydroxyethyl ether, ethanolamine, ethylenediamine, hexamethylenediamine and 2 methyl-pentamethylene diamine. The most preferred chain extender is water.

The preferred blowing agent is carbon dioxide, formed when water reacts with isocyanate groups. Any other conventional blowing agent as known in the polyurethane foam art may be used alone or in combination with carbon dioxide. Suitable supplementary or alternative blowing agents are methylene chloride, fluorocarbons, and fluorochlorocarbons.

Foam stabilizers are conventional in foam technology and serve to regulate cell size and prevent collapse of the foam cells by reducing the surface energy between the cell wall and the gas (air, carbon dioxide) in the cell. Foam stabilizers are usually surfactants, and, in the present invention, any surfactant as known in the foam art may be used, such as the polyoxyethylene ethers and esters of the Triton ® and Tween series. A preferred foam stabilizer is a silicone surfactant which may be included in the foam at a concentration of about 0.1 to 3.0% by weight.

While the germicidal component of the invention will henceforth be described in terms of the preferred P-I, the polyurethane foam sponge of the invention is not limited to P-I. Any germicidal agent which can form a water soluble, solid, particulate complex with a polymer is suitable for the invention. PEO is an example of a suitable polymer alternative to PVP, and alternative germicidal agents which form solid complexes with PEO and PVP are chlorhexidine, hexachlorophene, parachlorometaxylenol and quaternary ammonium compounds. If PEO is used as the water soluble polymer, it may have a molecular weight of about 100,000 to 8,000,000 (available from Union Carbide Corp. under the trade name Polyox ®).

PVP is a liquid, gum or glass having an intrinsic viscosity which depends on the molecular weight. Various molecular weight grades of PVP are conventionally identified in commerce via K values wherein K15, K30, K60 and K90 refer to molecular weights of about 10,000 50,000 150,000 and 350,000 respectively and to intrinsic viscosities of about 0.02 0.225, 0.75 and 1.61 respectively. In accordance with the present invention suitable PVP may have a K value of about 15 to 60, preferably about 30.

P-I, on the other hand, is an amorphous solid containing about 1 to 40% by weight of iodine. It may be prepared as a powder having any desired particle size. While the invention contemplates inclusion of P-I of any iodine percentage, it is preferred to use material having from 9 to 12% of available iodine as defined by the United States Pharmacopeia (USP). USP P-I is available commercially from GAF and BASF. It is understood that P-I having an iodine percentage different from that commercially available may easily be prepared by any convenient procedure as known in the art.

P-I, while instantly soluble in water, is not readily soluble in a mixture of the polyglycol and water. This observation provides a facile one step bulk polymerization route to the flexible foam of the invention having solid particles of P-I evenly dispersed throughout the foam. Thus, a mixture of the polyglycol and water, optionally containing a surfactant, a chain extender and a conventional polyurethane foam catalyst, such as dibutyl tin dilaurate or a tertiary amine, may be prepared and the solid particles of P-I suspended uniformly in the mixture by any convenient mixing procedure. The isocyanate component may be added to this mixture with rapid stirring. After the exotherm has peaked and the foam has risen substantially completely (about 1 to 15 minutes), the foam may be cured in an oven at about 125° C. for about 15 to 60 minutes, then cut into slabs of the desired shape in accordance with the intended use, such as a sponge or wound dressing.

The composition may include about 1 to 50, preferably about 5 to 20, most preferably about 9 to 15 percent by weight of the solid P-I particles.

When the foam sponge is wetted, water is instantly taken up into the foam cells where it contacts and dissolves the P-I particles in the foam matrix. As shown in Example IV, iodine is liberated into the aqueous medium in less than one minute. Preferably, a detergent solution is used to wet the sponge. When the sponge is wetted with detergent solution, a solution containing detergent and a high concentration of iodine is available for scrubbing with the sponge in a matter of seconds.

Alternatively, the sponge may be supplied to the user with detergent impregnated therein. Thus, a water soluble detergent may be included in the polyglycol mixture so that it becomes evenly dispersed in the foam matrix and releasable into water along with the P-I.

The foam of the invention and its compositional difference from a prior art foam are further illustrated with the aid of the drawings. FIG. 1 shows a section of the foam matrix 10 of the invention fabricated of molecules of polyurethane 12. Molecules 12 define foam cells 14 therebetween which may be open cells and/or closed cells as is well-known in the foam art. Solid particles 16 of P-I are dispersed evenly within matrix 10 with substantially no complexation between the PVP component of particles 16 and polyurethane molecules 12.

Figure 2:
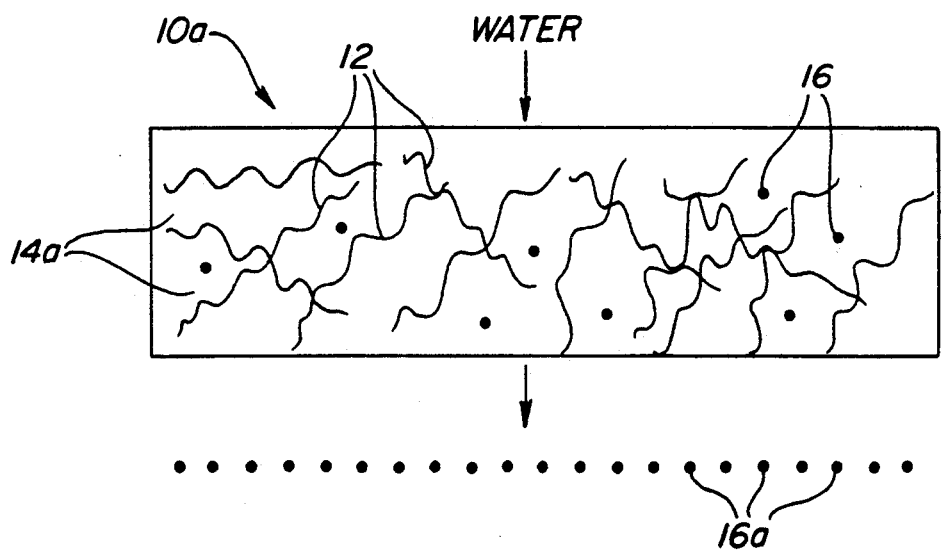
FIG. 2 illustrates the sponge of FIG. 1 after contact with water.

FIG. 2 illustrates foam matrix 10a after contact with water. (In the present disclosure, like elements in different drawings are given the same reference number followed by a lower case letter). The water enters cells 14a and contacts particles 16. Because of the high solubility of P-I in water and the substantial lack of complexation between the PVP in the solid particles and polyurethane molecules 12, the P-I particles dissolve almost instantaneously and migrate in a matter of seconds into the aqueous phase as P-I molecules 16a where they are available as disinfectant for scrubbing.

Figure 3:
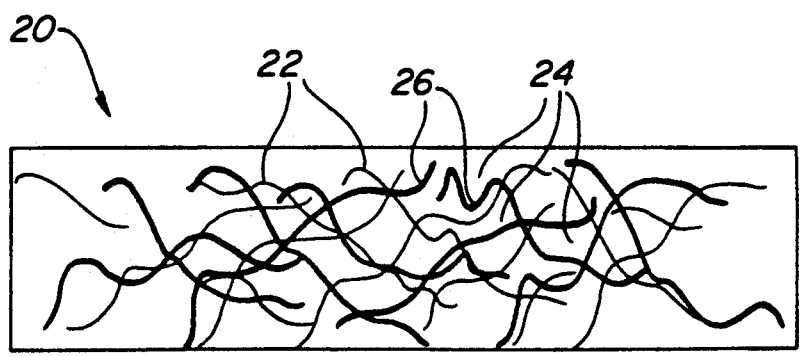
FIG. 3 illustrates a sponge of the prior art.
Figure 4:
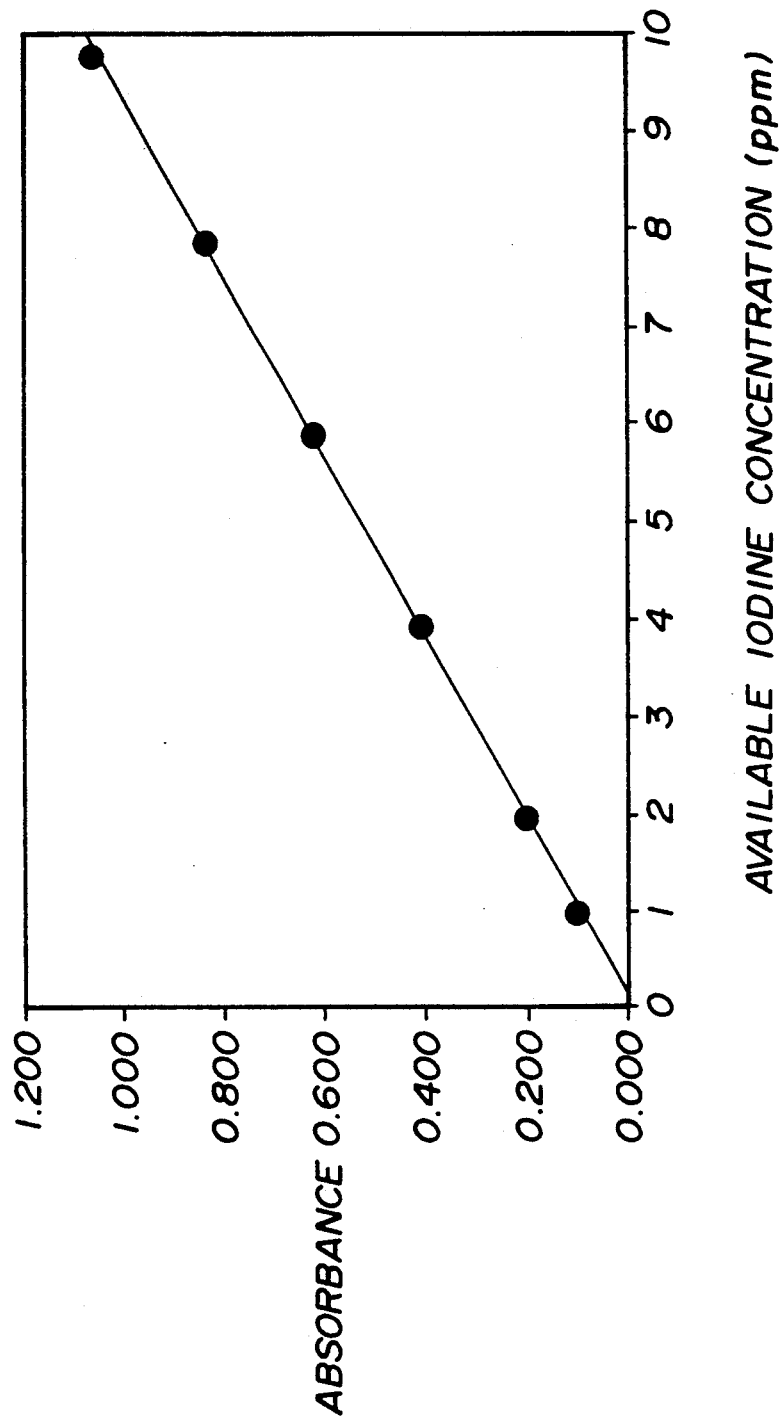
FIG. 4 is a plot of iodine concentration versus absorption at 352 nm.
Figure 5:
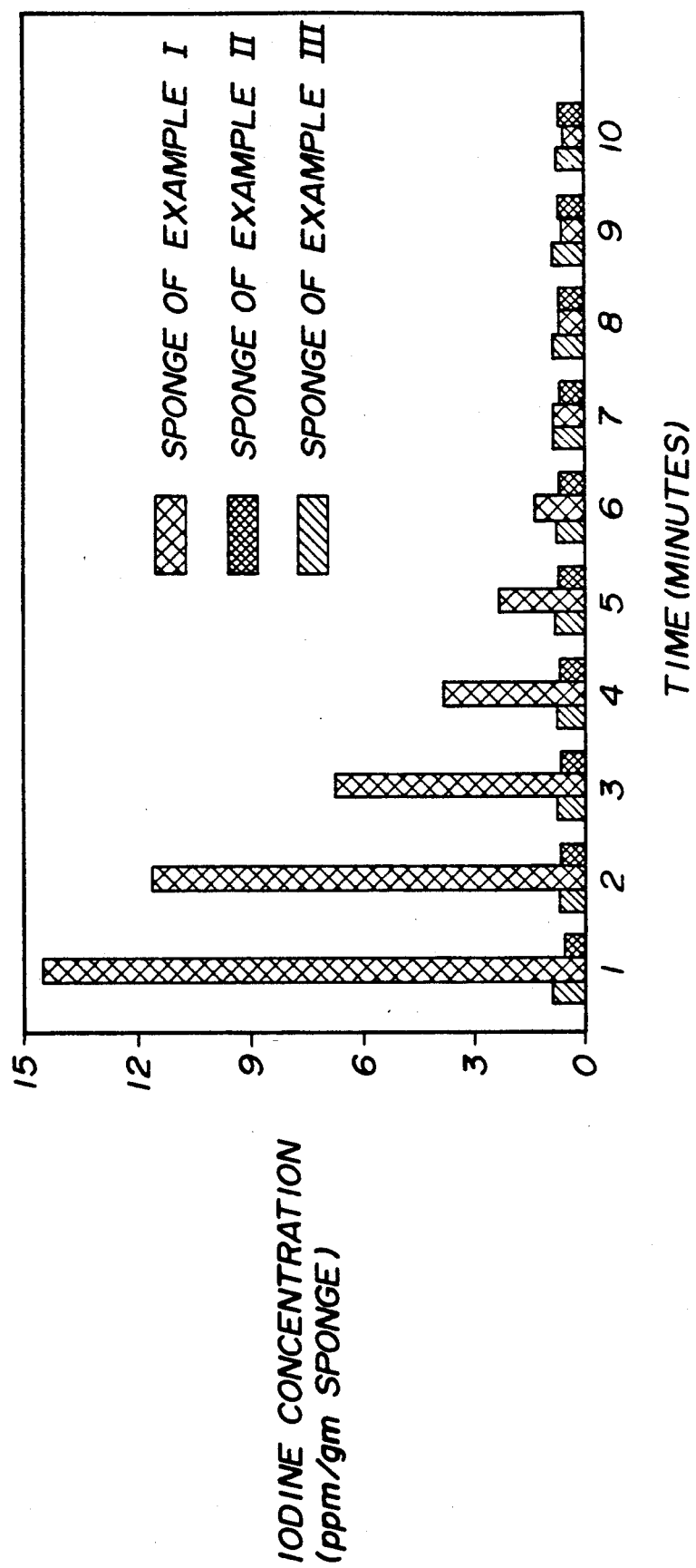
FIG. 5 compares the rate of iodine release from the foam sponge of the invention to a prior art foam sponge.

In contrast, FIG. 3 illustrates an IPN molecular complex polyurethane P-I foam composition of the prior art. Polyurethane foam matrix 20 consists of polyurethane molecule 22 defining foam cells 24. Individual molecules 26 of PVP are complexed with the polyurethane molecules at the molecular level in an IPN composition. PVP molecules 26 have iodine complexed thereto (not shown in the drawing). Because association of the polyurethane and PVP at the molecular level is very strong in the IPN configuration, release of the P-I, when foam 20 is contacted with water, is very slow. Further, the PVP of prior art foam 20 is of high molecular weight (K 85 or higher). The long chains of the high molecular weight PVP intertwine and complex particularly strongly with polyurethane molecules 22 further retarding release of P-I.

While the composition of the invention is preferably prepared as the foam described above, formulations other than foam, such as a germicidal melt having solid particles of P-I in polyurethane are contemplated. For use as a melt, the components of the polyurethane are a diisocyanate, a diol chain extender and a polyether glycol, preferably MDI, BDO, PEG or PTMEG or mixtures thereof. The germicidal melt may be prepared by suspending the solid P-I particles in a mixture of the extender and glycol prior to adding the isocyanate. A melt thus prepared may be coated onto a medical article, such as a catheter, merely by dipping the article into the melt. Preferably, the melt may be molded into an article of any desired shape. A particularly preferred molded article is a bristle for a scrub brush. Because of its free (uncomplexed) nature, the water soluble P-I particle is rapidly released when the brush is wetted with water, or, preferably with a detergent solution.

The sponge or brush of the invention may be included in a plastic package of sterilized materials for surgical scrubbing. The sponge may be supplied as a wet pack with sufficient detergent impregnated therein for a complete pre-operative scrubbing procedure, and may include brush bristles as a further scrubbing aid. Combination sponge and bristle scrubbing articles are well known in the art, for example the E-Z Scrub ® system sold by the Deseret Medical Division of Becton, Dickinson and Company, Sandy, Utah. Alternatively, and preferably, the package containing the sponge or brush may be supplied as a dry package to be used with any conventional detergent. The dry package may optionally include the detergent, dry or liquid, in a separate container. Other components useful for surgical scrubbing, such as a nail cleaner and paper or cloth wipes, may be included in the package.

The following examples are provided to further describe the invention but are not to be considered as limitative of the invention.

EXAMPLE I

Preparation of P-I Polyurethane Foam of the Invention

The P-I containing dry polyurethane flexible foam was prepared using the Bayfit 550 flexible foam system. Fifty parts (by weight) of Bayfit 550 polyether glycol component B and 6.73 parts by weight of P-I dry powder (Aldrich, available iodine approximately 10%) were placed in a mold cup and mixed well to form a uniform slurry. Bayfit 550 isocyanate component A, 17.25 parts by weight, was added at room temperature and the slurry was stirred vigorously until the onset of the foaming process. The foam curing process was continued for 30 minutes at ambient conditions and then post cured at 125° C. for 30 minutes The skin of the P-I containing dry flexible foam slab was removed and the desired sizes of sponges cut from the slab foam.

COMPARATIVE EXAMPLE II

A polyurethane/P-I IPN molecular complex sponge was prepared in accordance with Example 2 of the aforementioned U.S. Pat. No. 4,769,013. Pieces of this sponge were contacted for up to 15 minutes with distilled water using a syringe as described in Example IV. These solutions gave no detectable color in the conventional starch test indicating very low release of iodine over the time period of this experiment.

It is believed, although not substantiated, that this sponge releases the iodine slowly, as described in the referenced patent, because of the molecular complexation which results when the polyurethane and PVP are combined in solution.

COMPARATIVE EXAMPLE III

Preparation of P-I/Polyurethane IPN Molecular Complex Foam

A P-I/polyurethane molecular complex foam was prepared using Hypol 2002 hydrophilic prepolymer. Three parts (by weight) of solid P-I (Aldrich) were dissolved in 25 parts by weight of distilled water and added to 30 parts by weight of Hypol 2002 hydrophilic polyurethane prepolymer (W. R. Grace Co., Lexington, Massachusetts) in a mold cup and stirred vigorously until the onset of the foaming process. The foam curing process was continued for two hours at ambient conditions. The skin of the molecular complex foam slab was removed and the desired sizes of the sponges cut from the slab foam.

EXAMPLE IV

Iodine Release Rate Study

Iodine release rate of the sponges was determined using ultraviolet (UV) absorption due to triiodide ion. First, a standard iodine calibration plot was prepared. Known concentrations of P-I in 0.5 M KI were prepared and their UV absorbance at 352 nm due to triiodide was determined. A standard calibration plot was prepared based on these absorbances versus iodine concentration values (FIG. IV). Available iodine of the P-I (Aldrich) utilized in the standard calibration was determined using sodium thiosulfate titration.

Pieces of the sponges (0.8 gm) of Examples I, II and III were placed in 30 cc disposable syringe. Distilled water (15 ml) was drawn into the syringe and maintained in contact with the foam for one minute, then the solution was ejected from the syringe into an amber colored 30 ml bottle. This process was repeated nine additional times on the same sponge. Triiodide solutions were prepared by adding 1 ml of 0.5 M KI to 9 ml of the aqueous P-I solution from each extraction. The triiodide absorbance at 352 nm was measured and converted to released iodine concentration using the standard calibration plot. The results of this experiment are illustrated in FIG. V.

It is seen that the iodine release from the sponge of the invention (Example I) is significantly faster than that from the P-I polyurethane IPN molecular complex sponge (Examples II and III). In particular, a 15 fold increase in iodine release in the first minute is achieved.

Figure 6:
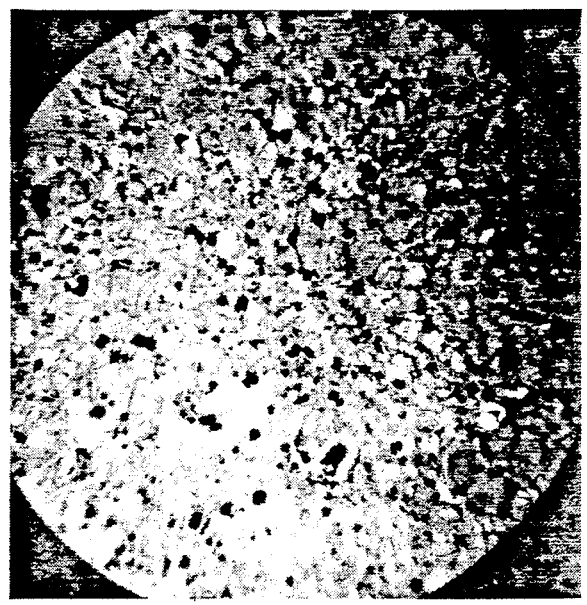
FIG. 6 is an optical micrograph of the foam sponge of the invention.
Figure 7:
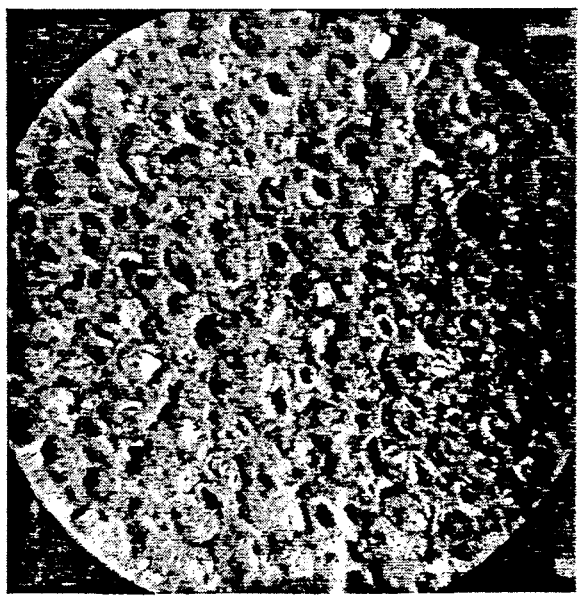
FIG. 7 is an optical micrograph of a prior art foam sponge.

The iodine release rates are consistent with the particle versus IPN form of the P-I in the sponges, as shown in the optical micrographs of FIGS. 6 and 7. FIG. 6 shows solid (uncomplexed) P-I particles in the sponge of the invention (Example I). No solid particles are seen in the sponge of Example III because of the dispersion of the PVP chains in the IPN network.

What is claimed is:

1. A composition comprising a polyurethane foam having dispersed evenly therein solid particles of a complex of polyvinylpyrrolidone and iodine, said polyurethane comprising the reaction product of a diisocyanate, polyglycol and water, said polyurethane and polyvinylpyrrolidone being substantially uncomplexed so that said foam, when contacted by an aqueous liquid, instantaneously releases said complex into said liquid.

2. The composition of claim 1 wherein said diisocyanate is selected from the group consisting of 4,4'-diphenylmethane diisocyanate, 3,3'-diphenylmethane diisocyanate, toluene diisocyanate isophorone diisocyanate, 4,4'-dicyclohexylmethane diisocyanate, and hexamethylene diisocyanate.

3. The composition of claim 1 wherein said toluene diisocyanate is selected from the group consisting of the 2,4-isomer, the 2,6-isomer and a mixture thereof.

4. The composition of claim 1 wherein said polyglycol is selected from the group consisting of a polyether glycol, polyester glycol, fluorinated glycol, silicone glycol and a mixture thereof.

5. The composition of claim 1 further comprising a component selected from the group consisting of a chain extender, a foam stabilizer, a detergent and a blowing agent.

6. The composition of claim 5 wherein said chain extender is selected from the group consisting of 1,4-butanediol, ethylene glycol, diethylene glycol; triethylene glycol; 1,2-propanediol; 1,3-propanediol; 1-6-hexanediol; trimethylol propane, 1,4-bis-hydroxymethyl cyclohexane, hydroquinone dihydroxyethyl ether, ethanolamine, ethylenediamine, hexamethylenediamine and 2-methylpentamethylene diamine and a mixture thereof.

7. The composition of claim 5 wherein said blowing agent is selected from the group consisting of carbon dioxide, methylene chloride, a fluorocarbon and a fluorochlorocarbon.

8. The composition of claim 1 wherein said polyvinylpyrrolidone has a K value of about 15 to 60.

9. The composition of claim 1 wherein said particles contain about 1 to 40% by weight of iodine.

10. The composition of claim 1 containing about 5 to 15 weight percent of said particles.

11. The composition of claim 1 in the form of a sponge.

12. The composition of claim 1 in the form of a wound dressing.

13. A composition comprising a polyurethane having dispersed evenly therein solid particles of a complex of a water soluble polymer and a germicidal agent, said polyurethane and said water soluble polymer being substantially uncomplexed so that said composition, when contacted by an aqueous liquid, instantaneously releases said complex into said liquid.

14. The composition of claim 13 wherein said water soluble polymer is selected from the group consisting of polyethylene oxide and polyvinylpyrrolidone.

15. The composition of claim 13 wherein said germicidal agent is selected from the group consisting of iodine, chlorhexidine, hexachlorophene, parachlorometaxylenol and a quaternary ammonium salt.

16. The composition of claim 13 in the form of a coating on a medical article.

17. The composition of claim 13 in the form of a bristle.

18. A package comprising materials for surgical scrubbing including a sponge fabricated from a polyurethane foam comprising a diisocyanate, polyether glycol and water, said polyurethane having solid particles of a complex of polyvinylpyrrolidone and iodine incorporated in the foam matrix thereof, said polyurethane and polyvinylpyrrolidone being substantially uncomplexed so that said foam, when contacted by an aqueous liquid, instantaneously releases said complex into said liquid.

19. The package of claim 18 further comprising a detergent.

20. The package of claim 19 wherein said detergent is in said foam.

21. The package of claim 18 further comprising a bristle.

22. The package of claim 18 further comprising a nail cleaner.

23. The package of claim 18 further comprising a wipe.

* * * * *